United States Patent [19]
Finkelstein et al.

[11] 4,328,209
[45] May 4, 1982

[54] CHOLERA VACCINE

[75] Inventors: Richard A. Finkelstein; Takeshi Honda, both of Dallas, Tex.

[73] Assignee: Board of Regents, The University of Texas System, Austin, Tex.

[21] Appl. No.: 29,092

[22] Filed: Apr. 11, 1979

[51] Int. Cl.$^3$ .................. A61K 39/106; C12N 15/00; C12N 1/36; C12R 1/63
[52] U.S. Cl. ...................................... 424/92; 435/172
[58] Field of Search .......................... 424/92; 435/172

[56] References Cited

U.S. PATENT DOCUMENTS

| | | | |
|---|---|---|---|
| 3,145,144 | 8/1964 | Ando | 424/92 |
| 3,328,253 | 6/1967 | Watanabe | 424/92 |
| 3,329,573 | 7/1967 | Hoerlein | 424/92 |
| 3,972,858 | 8/1976 | Stark et al. | 424/92 |
| 4,125,492 | 11/1978 | Cautrecasas | 424/92 |
| 4,264,737 | 4/1981 | Murphy | 435/172 |

FOREIGN PATENT DOCUMENTS

| | | | |
|---|---|---|---|
| 737281 | 2/1970 | Belgium | 424/92 |
| 1452648 | 10/1976 | United Kingdom | 424/92 |
| 2000028 | 1/1979 | United Kingdom | 424/92 |

OTHER PUBLICATIONS

Finkelstein, "Cholera" CRC Critical Reviews in Microbiology, May 1973, pp. 553-623, Esp., pp. 589-590, F.N. 391-404, Genetic Regulation, 599, F.N. 489-506, Oral Living Attenuated Cholera Mutant Vaccine.
Woodward et al., Proc. 11th Joint Conf. Cholera U.S.-Japan Medical Science Program (1975), 330-335, "Efficacy of a Live Oral Cholera Vaccine in Human Volunteers".
Chem. Abstracts, vol. 89 (1978)-vol. 56 (1962), Index Entry "Vibrio-Comma (Cholera), Eltor".
Chem. Abstracts, vol. 89 (1978)-vol. 56 (1962), Index Entry "Guanidine, 1 Methyl-3 nitro-1-nitroso".
C.A. 89:204042n, 1010c88:131408d, 166344g (1978), 87:63410a (1977) 81:35454a (1974).
C.A. 80:44287e (1974), 77:143756(b), (1972), 72:63879a (1970), 55:16676, 15583 (1961).
Finkelstein et al., J. Exp. Med. 130:185-202, (1969), "Pathogenesis of Experimental Cholera".
Nelson et al., Inf. & Immun. 14(2):527-547, Aug. 1976 "Vibrio cholerae Adherence and Colonization in Experimental Cholera: Electron Microscopic Studies".
WO80/02504, Published with Amended claims, Dec. 11, 1980, PCT/US80/00613, Oeschger; Max et al., "Genetically Attenuated Bacterial Vaccines with Multiple Mutations of the Same Phonotype".
Clements, J. D.; Finkelstein, R. A., "Demonstration of Shared and Unique Immunological Determinants in Entero Toxins from Vibrio-cholerae and Escherichia-coli", Infect. Immun. (Infib), V 22 (3), 1978, pp. 709-713, ISSN 00199567.
Clements, J. D.; Finkelstein, R. A., "Immunological Cross-Reactivity Between a Heat-Labile Entero Toxin(s) of Escherichia-coli and Subunits of Vibrio-cholerae Entero Toxin", Infect. Immun. (Infib), V 21 (3), 1978, pp. 1036-1040, ISSN 00199567.
Finkelstein, R. A.; Boesman-Finkelstein M., "Cholera and Related Diarrhoeas ('Turista')", Nature 275 (5677): 173-174, Sep. 78.
Klapper, David G.; Finkelstein, R. A.; Capra, J. Donald, "Subunit Structure and N-Terminal Amino Acid Sequence of the Three Chains of Cholera Enterotoxin", Immunochemistry (IMCHZ), V 13 (7), pp. 605-611, 1976.
Finkelstein, R. A., "Cholera Enterotoxin", Microbiology (Washington, D. C.), (MICRDG); pp. 236-241, 1975.
Finkelstein, R. A., "Cholera Enterotoxin (Choleragen)", Jpn. J. Med. Sci. Biol. (JJMCAQ), V 28 (1), pp. 76-78, 1975.
Finkelstein, R. A.; Boesman, Mary; Neoh, Sim Hee; LaRue, Michael K.; Delaney, Robert, "Dissociation and Recombination of the Subunits of the Cholera Enterotoxin (Choleragen)", J. Immunol. (JOIMA3), V 113 (1), pp. 145-150, 1974.
Holmes, R. K.; Vasil, M. L.; Finkelstein, R. A., "Isolation and Preliminary Characterization of Nontoxinogenic Mutants of Vibrio-cholerae", Abstr. Annu. Meet. Am. Soc. Microbiol. (ASMAC), V 73, 1973:90.
Peterson, J. W.; Lo Spalluto, J. J.; Finkelstein, R. A., "Localization of Cholera Toxin In-Vivo", J. Infect. Dis. (JIDIA), V 126 (6), 1972, 617-628.
Finkelstein, R. A.; La Rue, M. K.; Lo Spalluto, J. J., "Properties of the Cholera Exo Entero Toxin Effects of Dispersing Agents and Reducing Agents in Gel Filtration and Electrophoresis", Infect. Immun. (Infib), V 6 (6), 1972, 934-944.
Fujita, K.; Finkelstein, R. A., "Anti Toxic Immunity in Experimental Cholera Comparison of Immunity Induced Per Orally and Parenterally in Mice", J. Infect. Dis. (JIDIA), V 125 (6), 1972: 647-655.
Finkelstein, R. A.; Fujita, K., "Per Orally Induced Anti Toxic Immunity Against Cholera", Fed. Proc. (FEPRA), V 31 (2), 1972: 802.
Finkelstein, R. A.; Lo Spalluto, J. J., "Crystalline Cholera Toxin and Toxoid", Science (Wash D.C.) (SCIEA), V 175 (4021), 1972: 529-530.
Lo Spalluto, J. J.; Finkelstein, R. A., "Chemical and Physical Properties of Cholera Exo-Entero-Toxin (Choleragen) and its Spontaneously Formed Toxoid (Choleragenoid)", Biochem. Biophys. ACTA (BBACAQ), V 257 (1), 1972: 158-166.
Finkelstein, R. A.; Fujita, Koichiro; Lo Spalluto, J. J., "Procholeragenoid. Aggregated Intermediate in the Formation of Choleragenoid", J. Immunol. (JDIMA3), V 107 (4), pp. 1043-1051, 1971.
Finkelstein, R. A.; Peterson, J. W.; Lo Spalluto, J. J., "Conversion of Cholera Exo-Enterotoxin (Choleragen) to Natural Toxoid (Choleragenoid)", J. Immunol., 106 3, pp. 868-871, 1971.
Finkelstein, R. A.; Lo Spalluto, J. J., "Production of Highly Purified Choleragen and Choleragenoid", J. Infec. Dis. 121 Suppl. S63-S72, 1970.
Finkelstein, R. A., "Role of Choleragen in the Pathogenesis and Immunology of Cholera", Tex. Rep. Biol. Med. 27 Suppl. 1 181-201, 1969.

Vasil, M. L.; Holmes, R. K.; Finkelstein, R. A., "Conjugal Transfer of a Chromosomal Gene Determining Production of Enterotoxin in *Vibrio cholerae*", Science, V 157, pp. 849–850, 1975.

Finkelstein, R. A.; Vasil, M. L.; Holmes, R. K., "Studies on Toxinogenesis in *Vibrio cholerae*. I. Isolation of Mutants with Altered Toxinogenicity", J. Infect. Dis. (JIDIA), V 129 (2), 1974, pp. 117–123.

Howard, Bruce D., "A Prototype Live Oral Cholera Vaccine", Nature, V 230, pp. 97–99, 1971.

*Primary Examiner*—Shep K. Rose
*Attorney, Agent, or Firm*—Arnold, White & Durkee

[57] ABSTRACT

*Vibrio cholerae*, Ogawa serotype, El Tor biotype, are subjected to the mutagenic N-methyl-N'-nitro-n-nitrosoguanidine (NTG). First generation mutants are screened for toxin production, and in particular the absence of "A" or enzymatically active subunit production and production of B (binding) subunit. Putative $A^-B^+$ mutants are again exposed to NTG and screened for the $A^-B^+$ characteristics. The formula of the native toxin molecule is usually $A^+B^+_{5-6}$, the formula for the molecule produced by the selected second generation mutant is $A^-B^+_{5-6}$. This mutant strain is used for production of a live attenuated vaccine which can be administered orally. The mutant has been found to induce immunity, in an experimental model system, against subsequent challenge with virulent cholera vibrios. Because of the immunologic relationship to other enterotoxins (such as the heat-labile enterotoxin of *Escherichia coli*), the mutant may also induce immunity to diarrheal diseases other than cholera. In fact, antiserum to the isolated toxin-related protein produced by the mutant has been shown to neutralize *E. coli* enterotoxin. The mutant may also be used for the production of "choleragenoid", the non-toxic, highly immunogenic B portion of the cholera enterotoxin (choleragen) without the complication of toxicity associated with the complete enterotoxin.

2 Claims, No Drawings

CHOLERA VACCINE

BACKGROUND OF THE INVENTION

The present invention relates to a cholera vaccine and, more particularly, to a cholera vaccine made from a *Vibrio cholerae* mutant.

The *Vibrio cholerae* enterotoxin contains two immunologically active areas designated A and B. The A region, or biologically active region, is responsible for the biologic effects of the toxin, namely, the activation of adenylate cyclase. The B region is responsible for binding to the host membrane receptor—the $G_{M1}$ ganglioside. Although the B region is immunologically closely related to the holotoxin ($AB_{5-6}$), it is non-toxic but highly immunogenic.

OBJECTS OF THE INVENTION

It is an object of the present invention to provide a safe, effective cholera vaccine obtained from a strain of *Vibrio cholerae* which is immunogenic but non-pathogenic. These and other objects of the present invention will be apparent from the following description.

SUMMARY OF THE INVENTION

Mutagenized *Vibrio cholerae* are screened for negative subunit A production by subculture onto agar containing antiserum to purified A subunit. Colonies producing A subunit will have a characteristic "halo" of immune precipitation around or under them after incubation. Those not having the halo are then plated onto agar containing antiserum to purified B subunit. Some of these appeared to produce B antigens in initial tests. However, the putative "A⁻B⁺" colonies, when tested in broth culture by Ouchterlony tests, gave some suggestion of A antigen production. One of these was subjected to a second mutagenesis. Of approximately 2,000 "second generation" mutants, one was found to produce B antigen, without detectable A, and its cultured supernatant fluid was found to be nontoxic in the Y-1 adrenal cell system. This mutant is designated as "Texas Star".

DETAILED DESCRIPTION

The *Vibrio cholerae* enterotoxin contains two immunologically active areas designated A and B. The A region, or biologically active region, is responsible for the biologic effect of the toxin, namely, the activation of adenylate cyclase in eukaryotic target (host) cells. The B region is responsible for binding to the host membrane receptor—the $G_{M1}$ ganglioside. Although the B region is immunologically closely related to choleragen, it fails to produce the biologic effects of the A region.

In view of the foregoing the concept was developed that a desirable organism for vaccine purposes would be one which produced the B region and no A region, or one which produced the B region and an altered, biologically inactive, A region. In an attempt to produce such a mutant, suspensions of *Vibrio cholerae* are treated with a mutagenic agent N-methyl- N'-nitro-N-nitrosoguanidine (NTG). The procedure used is similar to that described by Adelberg et al., Biophys. Biochem. Res. Commun., 18: 788-795 (1965) with the following variation. Appropriate dilutions of the suspension to yield isolated colonies are applied to the surface of a nutrient medium containing antiserum directed against the A region of the cholera enterotoxin. Colonies which fail to produce precipitation (A⁻) are tested in a similar manner on a nutrient medium containing antiserum directed against the B region of the cholera enterotoxin. Those colonies which produce a substantial precipitation thus indicating production of the B region of the cholera enterotoxin (B⁺) are tested further by more sensitive techniques to determine whether they are in fact "A⁻B⁺".

The putative mutants are cultivated in broth cultures under conditions suitable for production of cholera toxin and, following incubation, the culture supernatants are concentrated by membrane ultrafiltration and the concentrates are then tested in Ouchterlony (double diffusion immunoprecipitation) tests against the respective antisera for the presence of A and B antigens.

The culture supernatants are also tested for toxicity resembling that of intact cholera toxin by applying serial dilutions of the supernatants to cultured Y-1 mouse adrenal tumor cells. These cells respond to cholera enterotoxin and related enterotoxins with a characteristic alteration in their cellular morphology. This is an extremely sensitive test for cholera enterotoxin. For example, culture supernatants of the parent strains used in this effort can be diluted $1:3^8$ and still cause the distinctive morphologic changes in adrenal cells. Failure to cause this change in dilutions of culture supernatant greater than 1:3 is regarded as evidence that cholera toxin was not present. Mutants which meet these criteria are then tested in the sensitive infant rabbit model to determine:

(a) whether they cause symptoms resembling cholera;
(b) whether they have the ability to colonize the infant rabbit - that is, to multiply in the intestine of infant rabbit.

Candidate strains are further tested for their stability by evaluating these properties in cholera vibrios which have been isolated from infant rabbits in consecutive serial passages in additional infant rabbits. Since failure to produce symptomatology could mean either -

(a) that the mutant was stable; or
(b) that a "revertant" could not express itself in the presence of overwhelming numbers of the mutant, additional experiments are performed to evaluate stability:

(i) Small numbers (e.g., approximately 100 viable organisms) of the wild-type virulent parent cholera vibrios are mixed with large numbers (e.g., $10^9$ to $10^{10}$) of the mutant strain and inoculated into the baby rabbits. Evidence (symptoms) of cholera in these rabbits indicate that had a revertant developed, it could have expressed itself in the presence of large numbers of the mutant population.

(ii) Additionally, large numbers of colonies of cholera vibrios isolated from the infant rabbits infected with the mutant strain are tested in the mouse Y-1 adrenal cell system mentioned above to determine whether they have acquired the ability to produce larger amounts of toxin than the original mutant.

The strain selected for these studies was a strain, 3083, isolated from a patient in Viet Nam in 1964. This strain is an Ogawa serotype El Tor biotype cholera vibrio, in contrast to the hypertoxigenic *Vibrio cholerae* 569B, which had been used unsuccessfully, previously, and which is an Inaba serotype strain of the classical biotype. In our tests, the strain 3083 produces similar amounts of cholera enterotoxin to strain 569B; in fact, it produces more cholera enterotoxin than other strains of

*V. cholerae* of the El Tor biotype. The El Tor biotype has a number of advantages as a live vaccine strain: it is "hardier"; it survives better in nature; and it colonizes better than strain 569B or other strains of the classical biotype. The epidemiologic evidence indicates that El Tor vibrios have a much higher infection-to-case ratio than do classical cholera vibrios. Therefore, a mutant which retains these properties of the El Tor biotype is much more likely to disseminate under the unsanitary conditions of areas where diarrheal disease is endemic and to produce "herd immunity". It is to be understood, however, that other strains also may be employed.

Following the first NTG mutagenesis of this strain at 37° C., eight of the more than 2900 colonies examined appeared to be A⁻ on A antiserum agar. Five of these appeared to produce B antigen in initial tests, but three of the "A⁻B⁺" colonies, when tested in broth culture by Ouchterlony tests, gave some suggestion of A antigen production and two gave equivocal reactions. One of these was subjected to a second mutagenesis with nitrosoguanidine at 30° C. Of approximately 2000 "second generation" mutants, one was found to produce B antigen (without detectable A) and its cultured supernatant was found to be nontoxic in the Y-1 adrenal cell system. This mutant has been designated as "Texas Star". A culture of this mutant organism has been deposited without restriction with American Type Culture Collection, Rockville, Md. and has been assigned accession number ATCC 31503. Interestingly, most of the colonies developing after the second mutagenesis are found to produce A antigen, suggesting that either reversion had occurred, that the subculture consisted of a mixture of A⁺ and A⁻ bacteria, or that the first mutant colony produced some small amount of A which was not sufficient to cause a clearly detectable reaction under the colony.

From subculture of the Texas Star mutant on nutrient agar medium containing streptomycin, an antibiotic to which the parent strain is susceptible, it was possible to isolate another mutant (a derivative of Texas Star) which was resistant to (that is, which would produce colonies in the presence of) 20 $\mu$g/ml of streptomycin. This mutant is designated "Texas Star SR". The inclusion of this additional mutational genetic marker (in addition to its inability to produce the A region of cholera toxin while producing B region) serves to differentiate Texas Star SR from other El Tor vibrios of the Ogawa serotype and is useful as an independent marker to evaluate potential claims of "reversion". A culture of this mutant organism has been deposited without restriction with American Type Culture Collection, Rockville, Md. and has been assigned accession number ATCC 31498.

The Texas Star-SR mutant has been cultivated in moderate-scale fermentor cultures according to the same procedures used routinely for the production of cholera enterotoxin, and enterotoxin-related protein has been isolated from these fermentor cultures in the same manner as we use for the isolation of cholera enterotoxin. During these procedures, the antigenically active mutant protein behaves identically to choleragenoid. There is no evidence for a protein peak in those fractions which contain cholera toxin when the wild-type parent strain is processed by the same techniques; rather, only the choleragenoid-like peak is observed. When this protein is further purified according to techniques previously established, it behaves in an identical manner as choleragenoid; and in subsequent tests (disc electrophoresis, immunoelectrophoresis, sodium dodecyl sulphate polyacrylamide gel electrophoresis, and Ouchterlony tests) no differences between the mutant protein and reference choleragenoid are detected.

With regard to their stability, the mutant strains have shown no evidence of reversion during 16 serial passages involving more than 300 infant rabbits, and more than 800 colonies isolated from the infant rabbits have been tested and show no evidence of enhanced toxicity in the mouse Y-1 adrenal cell culture system.

The amount of choleragenoid produced in vitro is similar to that which is produced by the parent strain, if we consider only the B portion of the whole toxin molecule in the latter instance, as demonstrated by a sensitive and reproducible radial immunodiffusion (Mancini) test.

The Texas Star-SR mutant has been inoculated into the intestinal tract of chinchillas where it produced no symptoms of cholera. When these chinchillas were subsequently challenged with virulent cholera vibrios, in parallel with control chinchillas which had not previously been inoculated with the mutant, the chinchillas were found to be resistant (immune) to experimental cholera.

Antiserum prepared, in rabbits, against the purified mutant choleragenoid has been found to neutralize (at high dilutions) both *V. cholerae* enterotoxin and the heat-Labile enterotoxin of *Escherichia coli*, another important cause of diarrheal disease.

A vaccine containing the Texas Star mutant or the Texas Star SR mutant may be prepared by growing the mutant in one or more subcultures to increase the cell count, and lyophilizing the cells until used. The cells are then reconstituted with a suitable medium, e.g. distilled water, and divided into unit doses containing about $10^5$ cells or more, usually from about $10^6$ to about $10^{10}$ cells per dose. In the case of an orally administered liquid vaccine the dosage volume may be about 5 ml. The liquid oral vaccine is administered after giving the recipient an amount of an alkali effective to neutralize stomach acidity, e.g., about 2 grams of $NaHCO_3$. The vaccine may also be administered in the form of an enteric coated capsule containing an equal quantity of lyophilized Texas Star or Texas Star SR mutant cells.

The following example illustrates the present invention without, however, limiting the same thereto.

EXAMPLE

An inoculum ($10^5$ cells/ml) of *Vibrio cholerae* Ogawa serotype, El Tor biotype is precultured in 16 ml of syncase media with shaking at 37° C. for 6 hours. The culture is then centrifuged at 2,000×G for 20 minutes. The cells are resuspended in 9.5 ml of Tris-maleate buffer (sterilized by membrane filtration), pH 6.0. The cell count is $1.2 \times 10^7$/ml. A 1.0 ml solution of N-methyl-N'-nitro-n-nitrosoguanidine (NTG) (sterilized by membrane filtration) containing 1,000 $\mu$g/ml in distilled water is added to 9.0 ml of the resuspended cells. The resulting mixture is incubated at 37° C. for 25 minutes while shaking gently. The mixture is then centrifuged (2,000×G for 15 minutes). The cells are resuspended in 30 ml of syncase and again centrifuged at 2,000 × G for 15 minutes. The cells are resuspended in 9.0 ml of 20% glycerol tripticase soya broth (TSB). The cell count is $1.6 \times 10^5$/ml. The cells are tested by plating an aliquot on agar containing anti-A serum. Colonies which fail to produce halos are cultured on agar containing anti-B serum. Colonies which produce halos with anti-B serum are selected. If not tested immediately, the cells may be stored at −70° C.

An inoculum ($10^6$ cells/ml) of the selected culture is precultured on 30 ml of syncase media with shaking at 30° C. for 5 hours. The cell culture is then centrifuged at 2,000×G for 20 minutes. The cells are then resuspended in 9.5 ml of Tris-maleate buffer (sterilized by membrane filtration) pH 6.0. The cell count is $2.9 \times 10^9$/ml. A 1.0 ml solution of NTG (sterilized by membrane filtration) containing 1,000 μg/ml in distilled water is added to 9.0 ml of the resuspended cells. The suspension is incubated at 30° C. for 30 minutes while shaking gently. The suspension is then centrifuged at 2,000×G for 20 minutes. The cells are resuspended in 30 ml of syncase. The suspension is then centrifuged again at 2,000×G for 20 minutes. The cells are resuspended in 9.0 ml of 20% glycerol TSB. The cell count is $2.1 \times 10^8$/ml. The cell suspension may be stored at −70° C. until used.

What is claimed is:

1. A live, attenuated El Tor biotype, Ogawa serotype *Vibrio cholerae* vaccine comprising the mutant "Texas Star" or "Texas Star SR" *Vibrio cholerae* bacteria assigned accession No. ATCC 31503 and 31498 and both deposited without restriction with American Type Culture Collection, Rockville, Maryland, dispersed in a physiologically acceptable medium, which bacteria produce the nontoxic, highly immunogenic B portion of the cholera enterotoxin in substantially the same amount as virulent *Vibrio cholerae* bacteria while being substantially free of the A portion of the cholera enterotoxin capable of activating adenylate cyclase in a host cell.

2. A live, attenuated *Vibrio cholerae* vaccine in accordance with claim 1 which is effective to provide immunologic protection against diarrheal bacertial diseases including diseases induced by *Vibrio cholerae* and *Escherichia coli*.

UNITED STATES PATENT OFFICE
CERTIFICATE OF CORRECTION

Patent No. 4,328,209             Dated  May 4, 1982

Inventor(s)  Richard A. Finkelstein et al

It is certified that error appears in the above-identified patent and that said Letters Patent are hereby corrected as shown below:

(Col. 1, Line 5), add the following new paragraph:

-- The Government has rights in this invention pursuant to Research Grant No. AI-08877-11 awarded by the Department of Health, Education and Welfare. --

Signed and Sealed this

*Thirty-first* Day of *May 1983*

[SEAL]

*Attest:*

DONALD J. QUIGG

*Attesting Officer*   *Acting Commissioner of Patents and Trademarks*